United States Patent [19]

Bailey

[11] Plant 4,396

[45] Mar. 20, 1979

[54] ROSE PLANT

[75] Inventor: Dorothy J. S. Bailey, Bakersfield, Calif.

[73] Assignee: San Joaquin Rose Co., McFarland, Calif.

[21] Appl. No.: 903,382

[22] Filed: May 5, 1978

[51] Int. Cl.[2] ..... A01H 5/00

[52] U.S. Cl. ..... Plt./15

[58] Field of Search ..... Plt./15

*Primary Examiner*—Robert E. Bagwill

*Attorney, Agent, or Firm*—Vincent G. Gioia

[57] ABSTRACT

A novel rose variety of the hybrid tea class characterized by flowers of attractive yellow coloring and borne singly on sturdy stems substantially as shown and described.

1 Drawing Figure

1

The present invention relates to a new and distinct variety of rose plant of the hybrid tea class, which was originated by my crossing the rose variety known as "Golden Scepter" (U.S. Plant Pat. No. 910, now expired) as seed parent with the rose variety known as "Golden Masterpiece" (U.S. Plant Pat. No. 1,284, now expired) as pollen parent.

Among the novel characteristics possessed by this new variety which distinguish it from its parents and all other varieties of which I am aware are: (1) long, tapered, bright yellow flowers which combine deep yellow tones and are borne singly on sturdy stems, (2) well formed flowers with regularly arranged petals displaying a recurling effect, long lasting on the bush and as a cut flower and (3) an upright growing plant with abundant foliage. Asexual reproduction by budding of the new variety as performed in Kern County, Calif., shows that the foregoing and other distinguishing characteristics come true to form and are established and transmitted through succeeding propagations.

A main distinguishing feature of the new and improved rose variety is the very pleasant strong yellow coloring of the flowers which are produced in good size and in large quantities. In addition, this new variety is especially resistant and winter hardy for this color class.

Flowers of this new variety are usually borne singly, opening from long tapered buds of deeper yellow coloring with recurling petals as the bloom matures. Petals are of a velvety appearance and are regularly arranged, however, the flowers are long lasting on the plant and after cutting. The abundant, thick, leathery foliage provides a fine background for the distinctive and attractive yellow tonality of the blooms.

The accompanying drawing shows typical specimens of the flowers and vegetative growth of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "12B" is plate 12B of the Royal Horticultural Society Color Chart.

Parentage: Seedling.

*Seed parent.*—"Golden Scepter".

*Pollen parent.*—"Golden Masterpiece".

2

Class: Hybrid tea.

The following observations are made of specimens grown outdoors at Kern County, Calif., during the month of June.

I. FLOWER

Blooming Habit: Continuous.

A. Bud:

(1) *Size.*—Medium.

(2) *Form.*—Long, tapered.

(3) *Color.*—When sepals first divide — near 12A. When petals begin to unfurl — 12B. When half-blown: inside of petals — 10A; reverse side of petals — 11B.

(4) *Sepals.*—Thin, pointed, extending about two-thirds of the bud length.

(5) *Peduncle.*—Strength — erect.

B. Bloom:

(1) *Size.*—Average size when fully expanded 4 to 4½ inches.

(2) *Borne.*—Singly.

(3) *Form.*—Long tapered, well formed.

(4) *Petalage.*—Number of petals under normal conditions — about 34.

(5) *Color.*—Center of flower — 15D. Outer petals — 12C. Base of petals — 11A. Reverse of petals — 12C. General tonality from a distance — strong bright yellow 11A.

(6) *Color Change.*—As bloom ages — 11B. General tonality — 11B. After three or more days — 12C.

C. Petals:

(1) *Texture.*—Thick.

(2) *Appearance.*—Velvety both inside and outside.

(3) *Form.*—Long, pointed.

(4) *Arrangement.*—Regularly arranged, with recurling affect.

(5) *Petaloids in Center.*—Medium.

(6) *Persistence.*—Drop off clean.

(7) *Fragrance.*—Good.

(8) *Lasting quality.*—Long lasting on the plant and as a cut flower.

2. REPRODUCTIVE ORGANS

A. Stamens, Anthers:

(1) *Arrangement.*—Regularly arranged around styles.

(2) *Color.*—20B.

B. Pollen: Color — 20D.

C. Styles: Bunches; uneven length; thin.
D. Stigmas: Color — 20D.
E. Hips: Shape—globular, medium size. Color—168C when mature, seeds protrude.

3. PLANT

A. Form: Upright.
B. Growth: Upright with strong canes. Height attained — 3½ to 4 ft. during normal growing season.
C. Foliage: Compound of 5 to 7 leaves.
(1) *Size.*—Medium.
(2) *Quantity.*—Abundant.
(3) *Color.*—New foliage: upper side — 139A; under side — 137C. Old foliage: Upper side — 137A; under side — 138B.
(4) *Shape.*—Pointed.
(5) *Texture.*—Upper side — leathery, waxed. Under side — rough.
(6) *Edge.*—Serrated on points only.
(7) *Serration.*—Very small.
(8) *Leaf stem.*—Color — 147C; under side — 139C.
(9) *Stipules.*—Medium length; slightly bearded.
D. Wood:

(1) *New Wood.*—Color — 147B with dark bronze cast. Bark — smooth.
(2) *Old Wood.*—Color — 137D. Bark — rough.
E. Thorns:
(1) *Thorns.*—Quantity — ordinary, few on laterals. Form — flat. Length — small. Color when young — 174A. Position — regular.
(2) *Prickles.*—Quantity on main stalks — profuse; on laterals — medium.
F. Plant's Disease Resistance: Mildew — good. Black-spot — good. Rust — good.
G. Winter Hardiness: Winter hardy in most areas.

I claim:

1. A new and distinct variety of rose plant of the hybrid tea class, substantially as shown and described, characterized particularly by flowers of attractive yellow coloring borne singly on sturdy stems with regularly arranged petals displaying a recurling affect which are long lasting on the plant and as a cut flower and by a plant of upright habit of growth having an abundance of leathery, waxy foliage.

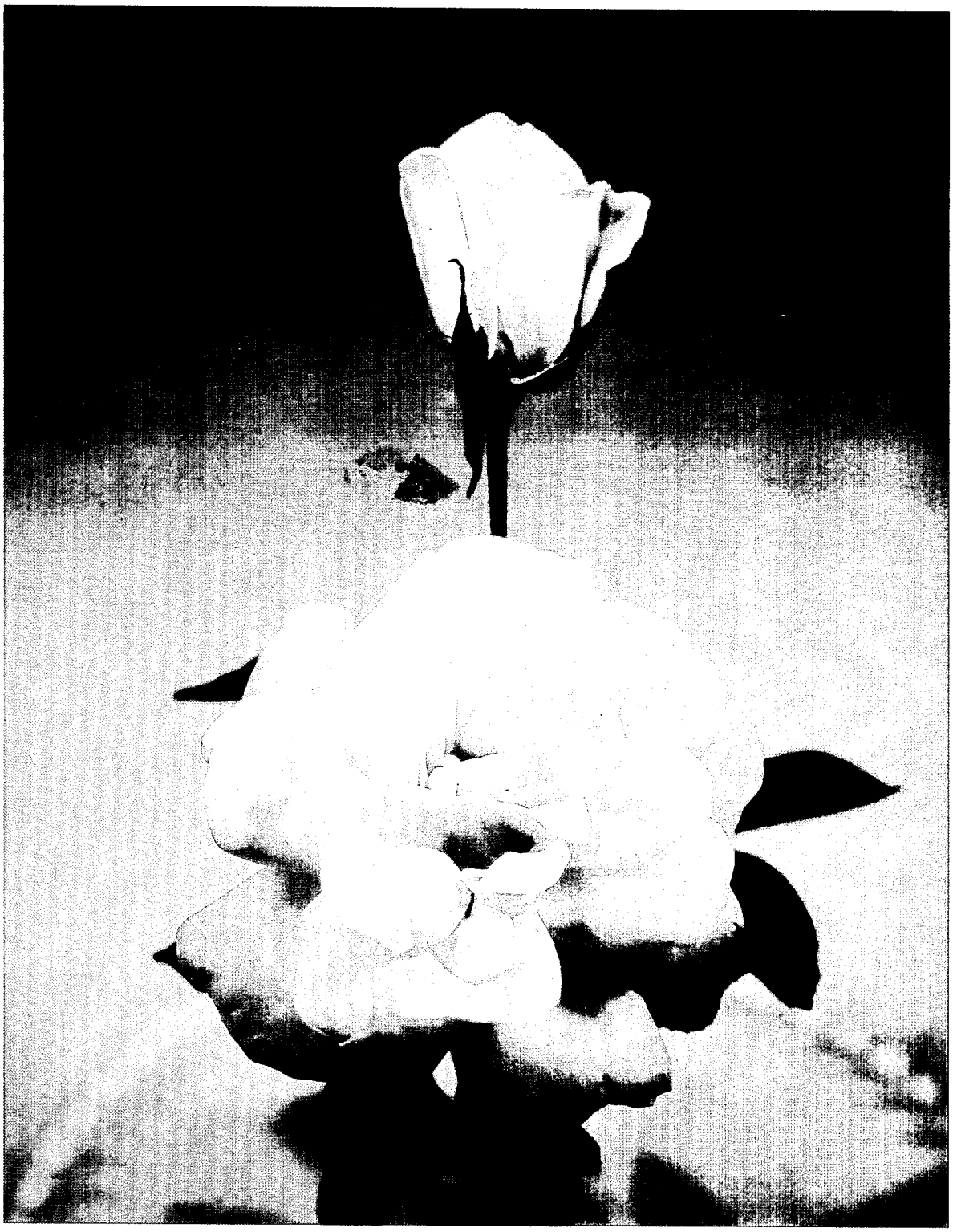

* * * * *